United States Patent [19]
Grainger et al.

[11] Patent Number: 5,998,137
[45] Date of Patent: Dec. 7, 1999

[54] METHODS OF DIAGNOSIS BY DETECTING POLYMORPHISMS IN THE TGF-β1 PROMOTER

[76] Inventors: David J. Grainger, 9 St Johns St., Duxford Cambridge, United Kingdom, CB2 4RA; Timothy D. Spector, 22 Aberdeen Rd, London, United Kingdom, N5 2VH; Kirsten Heathcote, 163 Water Street, Chesterton Cambridge, United Kingdom, CB4 1PB

[21] Appl. No.: 08/784,386

[22] Filed: Jan. 17, 1997

[30] Foreign Application Priority Data

Jan. 17, 1996 [GB] United Kingdom .................... 9600957
Aug. 23, 1996 [GB] United Kingdom .................... 9617674

[51] Int. Cl.$^6$ .............................. C12Q 1/68; C07H 21/04
[52] U.S. Cl. ............................ 435/6; 435/91.2; 435/810; 536/24.31; 536/24.33; 514/1
[58] Field of Search ............................... 435/6, 91.2, 810; 514/1; 536/24.31, 24.33; 935/78

[56] References Cited

U.S. PATENT DOCUMENTS 5,445,941  8/1995  Yang et al. .................................. 435/6
5,698,399  12/1997  Duff et al. .................................. 435/6

FOREIGN PATENT DOCUMENTS

WO 86/06102  10/1986  WIPO .
WO 93/01315  1/1993  WIPO .
WO 94/03633  2/1994  WIPO .
WO 95/15334  6/1995  WIPO .

OTHER PUBLICATIONS

Cardillo et al. Arch Cytol Pathology. 44:241–249, 1996.

Kim, S.–J. et al., "Characterization of the Promoter Region of the Human Transforming Growth Factor–β1 Gene," *J. Biol. Chem.* 264(1):402–408 (1989).

Kim, S.–J. et al., "Promoter Sequences of the Human Transforming Growth Factor–β1 Gene Responsive to Transforming Growth Factor–β1 Autoinduction, " *J. Biol. Chem.* 264(12):7041–7045 (1989).

Lafyatis, R. et al., "Structural and Functional Characterization of the transforming Growth Factor β3 Promoter," *J. Biol. Chem.* 265(31):19128–19136 (1990).

*Primary Examiner*—Carla J. Myers
*Attorney, Agent, or Firm*—Sterne, Kessler, Goldstein & Fox P.L.L.C

[57] ABSTRACT

A method of diagnosis comprises determining genotype of a TGF-β1 promoter-specific polmorphisms that have been identified are at positions –800bp and –509bp. The genotype determined is then used to assess predisposition or susceptibility to a number of diseases: osteoporosis, atherosclerosis, cancer and immune disorders.

19 Claims, 4 Drawing Sheets

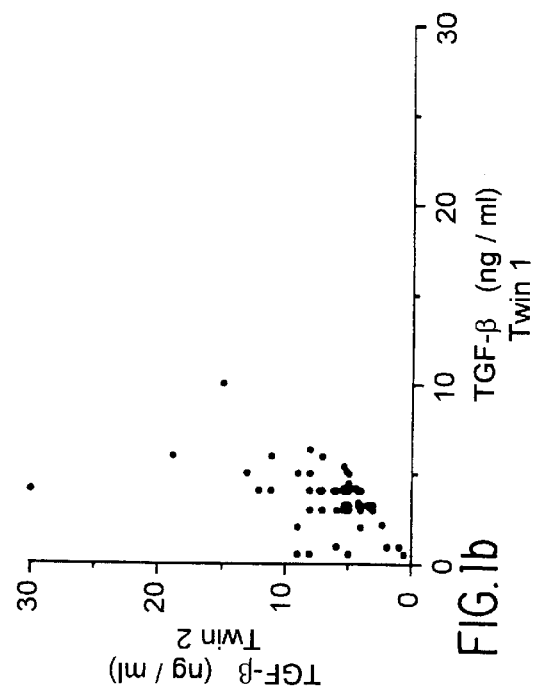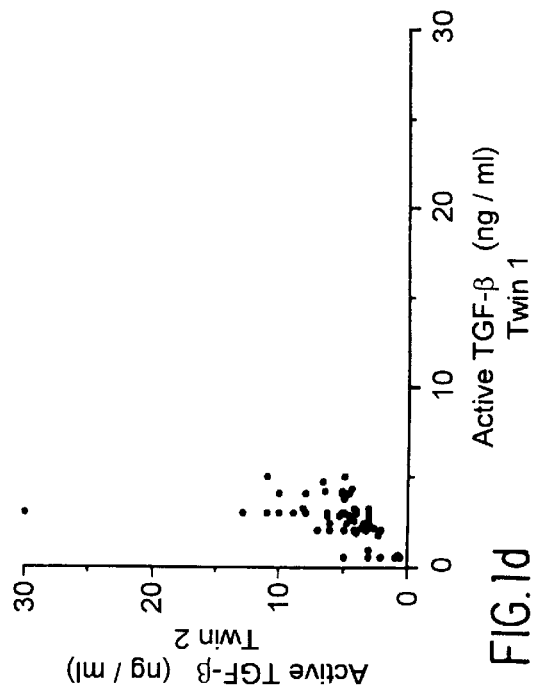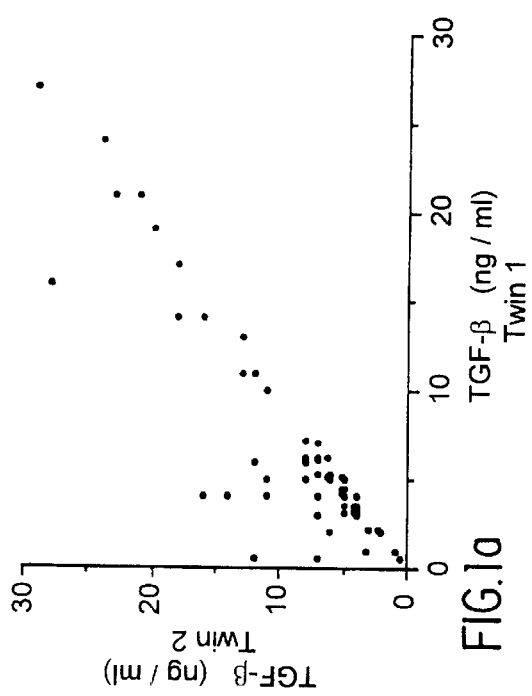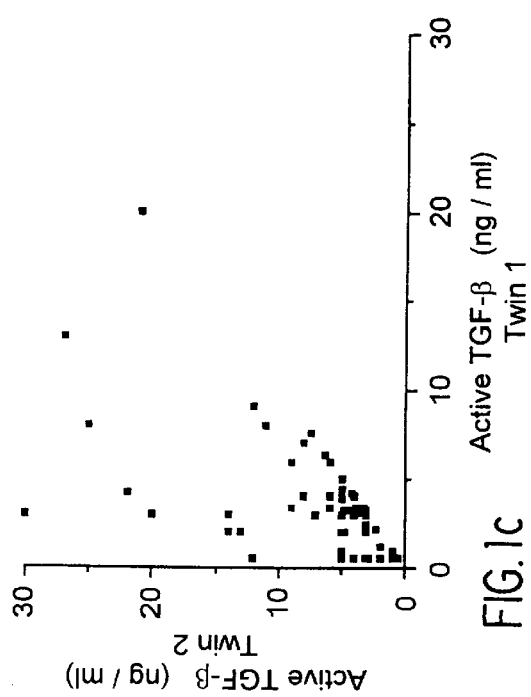

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

CCCGGCTCCA TTTCCAGGTG                                          20

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 2:

TGCTCTTGAC CACTGTGCCA                                          20

(2) INFORMATION FOR SEQ ID NO: 3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 3:

CAGACTCTAG AGACTGTCAG                                          20

(2) INFORMATION FOR SEQ ID NO: 4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 4:

GGTCACCAGA GAAAGAGGAC                                            20

(2) INFORMATION FOR SEQ ID NO: 5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

CTCTGCCTCC AACGTCACCA CCAT                                       24

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

CCCTTCCATC CCTCAGGTGT CCT                                        23

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

CTCTGCCTCC AACATCACCA CCAT                                       24

(2) INFORMATION FOR SEQ ID NO: 8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

CCCTTCCATC CTTCAGGTGT CCT                                        23

(2) INFORMATION FOR SEQ ID NO: 9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CTCTGCCTCC AACATCACCA CCATC                                      25

(2) INFORMATION FOR SEQ ID NO: 10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CTCTGCCTCC AACGTCACCA CCATC                        25

METHODS OF DIAGNOSIS BY DETECTING POLYMORPHISMS IN THE TGF-β1 PROMOTER

BACKGROUND OF THE INVENTION

1. Field of the Invention

This invention relates to diagnostic method and apparatus based upon a polymorphism in a TGF-β gene. More specifically, this invention relates to a method for diagnosis of pre-disposition to certain disease states, by screening for the presence of this polymorphism. The invention also relates to apparatus for screening for the polymorphism. The invention further relates to TGF-β genes containing the polymorphism and to a probe therefor.

2. Related Art

A number of major disease states are associated with or correlated with concentration of transforming growth factor β (TGF-β) in circulating plasma. Diseases that have been correlated in this way include atherosclerosis, certain forms of cancer, osteoporosis and a number of auto immune disorders, such as rheumatoid arthritis, multiple sclerosis, systemic lupus erythematosus, late on set diabetes and others.

In a number of cases, therapy is available for these disease states. However, a problem common to many of these therapies is that whilst the therapy is capable of halting further development of the disease, the therapy is nevertheless not capable of reversing or curing the diseased state to a significant extent.

Hormone replacement therapy is an established treatment for osteoporosis and has proved successful in halting further decline in bone density that is characteristic in women suffering from this disease. Hormone replacement therapy is generally not, however, able to bring about a reversal of osteoporosis, that is to say it is not capable of inducing an increase in the bone density of sufferers.

It would, accordingly, be of particular advantage to be able to identify with increased accuracy those individuals having a predisposition or increased susceptibility to osteoporosis. Suitable therapy could then be put into place before the effects of osteoporosis set in.

A similar situation obtains in respect of atherosclerosis and cancer. In the latter case, treatment of cancer often involves severe side effects. If it were possible to identify individuals with a predisposition or increased susceptibility to cancers then there would be advantage in providing those individuals with preventative therapy to reduce or prevent or delay the onset of cancer as part of a therapy having reduced side effects to those seen with the standard cancer treatments available.

SUMMARY OF THE INVENTION

The present invention relates to a method of diagnosis comprising determining genotype of a TGF-β1 promoter.

The invention also relates to a diagnostic means, comprising a means for determining genotype of a TGF-β1 promoter.

The invention also relates to a DNA molecule comprising a TGF-β1 gene in which the guanine at position −800bp is substituted by adenine. Preferably, the DNA molecule is an isolated DNA molecule.

The invention also relates to a method of osteoporosis therapy comprising, screening an individual for a genetic predisposition to osteoporosis; and if such a predisposition is identified, treating that individual to prevent or reduce osteoporosis or to delay the onset of osteoporosis.

The invention also relates to a method of atherosclerosis therapy comprising, screening an individual for a genetic predisposition to atherosclerosis; and if such a predisposition is identified, treating that individual to prevent or reduce atherosclerosis or to delay the onset of atherosclerosis.

The invention also relates to a method of cancer therapy comprising screening an individual for a genetic predisposition to cancer; and if such a predisposition is identified, treating that individual to prevent or reduce cancer or to delay the onset of cancer.

The invention also relates to a method of immune disorder therapy comprising, screening an individual for a genetic predisposition to immune disorder; and if such a predisposition is identified, treating that individual to prevent or reduce immune disorder or to delay the onset of immune disorder.

The invention also relates to a diagnostic kit comprising a carrier means being compartmentalized to receive in close confinement therein a means for determining genotype of a TGF-β1 promoter. Preferably, the means for determining the genotype is present in a container means.

BRIEF DESCRIPTION OF THE FIGURES

FIGS. 1A–1D show the circulating concentration of TGF-β in twin pairs. The concentration of active plus plasma latent TGF-β (1A, 1B) and active TGF-β (1C, 1D) was measured in serum from monozygotic (1A, 1C) and dizygotic (1B, 1D) twins. All individuals were female, post-menopausal and not receiving hormone replacement therapy. For each pair, twin 1 was arbitrarily designated as the sibling with lowest circulating concentration of TGF-β.

DETAILED DESCRIPTION OF THE PREFERRED EMBODIMENTS

Figure 2A:
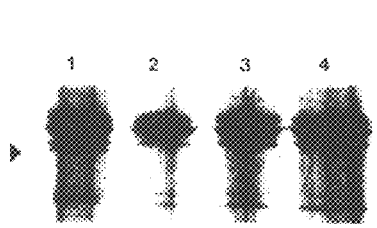
FIGS. 2A–2D show a polymorphism in the TGF-β1 promoter associated with circulating TGF-β concentration. (2A) Single strand conformation polymorphism (SSCP) acrylamide gel of non-denatured DNA obtained by polymerase chain reaction between primers 5'-CCCGGCTCCATTTCCAGGTG-3' (−1106 to −1125bp) (SEQ ID NO: 1) and 5'-TGCTCTTGACCACTGTGCCA-3' (−738p to −757bp) (SEQ ID NO: 2) with lymphocyte-derived genomic DNA from four healthy Caucasian donors as the template. One heterozygote (lane 1) is shown with the diagnostic doublet indicated by an arrow. (2B) Diagrammatic representation of the putative transcription factor binding sites in the TGFb1 promoter. Hatched box: one or more consensus sp1 binding sites; vertical line: consensus ap2 binding site; stippled oval: consensus glucocorticoid response element; filled box : consensus CREB half-site. The sequence of the CREB half-site is shown (boxed) with the single base polymorphism that resulted in the SSCP doublet shown in (1A) marked in bold script (SEQ ID NOS: 9 and 10). The maeIII consensus sequence present in the G allele (GTNAC) is underlined. All nucleotide positions are related to the most 5' transcriptional start site of the TGFb 1 gene described in *J Biol Chem.* 264:402–408 (1989). (2C) Distribution of circulating concentration of TGF-β in those twin pairs analyzed in FIG. 1A who have no A allele identified by the absence of undigested DNA in the maeIII digestion of the PCR fragment obtained in (1A) above. (2D) Distribution of the circulating concentration of TGF-β in individuals with AG genotype.

It is an object of this invention to provide method and apparatus for detecting individuals having a predisposition or susceptibility to certain disease states. It is a further object of the invention to identify individuals having such a predisposition or susceptibility by identifying those individuals with an altered TGF-β gene. It is another object of the invention to provide a therapy for those individuals have a predisposition or susceptibility to certain disease states. A still further object of the invention is to provide a therapy for those individuals having a predisposition or susceptibility to certain disease states that are correlated with concentration of TGF-β in circulation.

Accordingly, a first aspect of the invention provides a method of diagnosis comprising determining genotype of a TGF-β1 promoter.

The method of the invention typically comprises determining whether an individual is homozygous or heterozygous for a TGF-β1 promoter and a particular polymorphism thereof. The method is conveniently used to screen for an individual at risk of a condition or disease correlated with TGF-β deficiency, such as osteoporosis, or correlated with elevated levels of TGF-β, such as some cancers.

The DNA sequence of the TGF-β1 promoter region is known and has been published by Kim, S. J. et al, in *J. Biol. Chem.* 264 (1989) pages 402–408. This sequence is referred to hereafter as the wild type sequence or the published sequence. The method of the invention determines whether the individual being tested has a TGF-β1 promoter which is identical with the published sequence or whether that individual has a TGF-β1 promoter which differs from the published sequence, i.e. is a polymorphism of the published sequence. In carrying out the invention, an individual's TGF-β1 promoter genotype is generally determined by analysis of a section of the TGF-β1 promoter, rather than by analysis of the entire gene. If the sequence of that section is found to be the same as the corresponding section in the wild type sequence, then that individual is classified as having the wild type TGF-β1 promoter gene.

In use of a specific embodiment of the invention to be described below in further detail, an individual is screened to determine whether he or she possess a TGF-β1 promoter which is the published sequence or is a polymorphism thereof in which a guanine nucleotide at position −800bp has been replaced by an adenine nucleotide. In this specific embodiment, the presence of the polymorphism in which guanine is replaced by adenine at position −800bp correlates with a decreased level of TGF-β in circulation and with a predisposition to certain disease states. As examples of these disease states are included one or more of atherosclerosis, cancers, osteoporosis, rheumatoid arthritis, multiple sclerosis, systemic lupus erythematosus and other auto immune disorders.

Screening is carried out, for example, using PCR primers adapted to amplify a portion of the TGF-β1 gene that includes the nucleotide at position −800bp. It is preferred that the PCR primers are selected so as to amplify a region of the gene that surrounds position −800bp and includes at least six nucleotides on either side of this position. PCR techniques are well known in the art and it would be within the ambit of a person of ordinary skill in this art to identify primers for amplifying a suitable section of the TGF-β1 gene including position −800bp. PCR techniques are described for example in EP-A-0200362, EP-A-0201184, U.S. Pat. Nos. 4,683,195, 4,800,159 and 4,683,202.

In a specific embodiment of the invention described in further detail below, the PCR primers have the nucleotide sequences:

CCCGGCTCCATTTCCAGGTG (SEQ ID NO: 1) and
TGCTCTTGACCACTGTGCCA (SEQ ID NO:2).

The screening is suitably carried out by amplifying a DNA fragment including position −800bp of the TGF-β1 gene and determining whether the amplified region is cleavable by the restriction endonuclease maeIII. Cleavage by maeIII indicates that the gene is the wild type, while loss of cleavage by maeIII indicates that the gene is a variant form, i.e. a polymorphism. It is preferred that the PCR primers are selected so as to be homologous with a region of the genome within 1 kb of position −800bp on the TGF-β1 gene.

In a further embodiment of the invention, the diagnostic method comprises analysis of the TGF-β1 promoter using single strand conformational polymorphism (SSCP) mapping. It is preferred that the PCR primers are selected so as to be homologous with a region of the genome within 200bp of position −800bp on the TGF-β1 gene. It is further preferred that the PCR primers are selected so that position −800bp is substantially towards the middle of the amplified DNA segment.

In use of a further specific embodiment of the invention, described in greater detail below, an individual is screened to determine whether he or she possesses a TGF-β1 promoter which is the published sequence or is a polymorphism thereof in which a cytosine nucleotide at position −509bp has been replaced by a thymine nucleotide. In this specific embodiment, the presence of the polymorphism correlates with an elevated level of TGF-β in circulation and with a predisposition to certain disease states, associated with elevated circulating TGF-β, such as some cancers.

Screening may be carried out using PCR primers to amplify a portion of the TGF-β1 gene around position −509. Examples of suitable primers are:

CAGACTCTAGAGACTGTCAG (SEQ ID NO: 3) and
GGTCACCAGAGAAAGAGGAC (SEQ ID NO: 4).

The −509 polymorphism can be detected using Bsu 361, loss of cleaving indicating presence of the polymorphism.

Alternatively, the −509 polymorphism is detectable using SSCP techniques.

A second aspect of the invention provides diagnostic means comprising PCR primers adapted to amplify a region of a TGF-β1 promoter, preferably a DNA segment comprising a nucleotide at position −800bp, or a segment comprising position −509bp, on the TGF-β1 gene. It is preferred that the PCR primers are adapted to amplify a DNA segment that is up to 2kb in length, more preferably up to 1 kb in length.

In a particular embodiment of the invention the segment is approximately 400bp in length.

In specific embodiments of the invention described below, the PCR primers are (i) CCCGGCTCCATTTCCAGGTG (SEQ ID NO:1) and TGCTCTTGACCACTGTGCCA (SEQ ID NO:2), or (ii) CAGACTCTAGAGACTGTCAG (SEQ ID NO: 3) and GGTCACCAGAGAAAGAGGAC (SEQ ID NO: 4).

Optionally, the diagnostic means further comprises means to determine which nucleotide is found at position (a) −800bp or (b) −509bp on the TGF-β1 gene. Examples are the restriction endonuclease maeIII for (a) and the restriction endonuclease Bsu 36I for (b). As will be appreciated by a person of skill in the art, an alternative restriction endonuclease that is for example able to cleave the DNA segment when a guanine nucleotide is at position −800bp and is not able to cleave the segment when an adenine nucleotide is at position −800bp is also suitable. Alternatively, a suitable agent would cleave the segment when the nucleotide at position −800bp is adenine and not cleave the segment when this nucleotide is guanine, and likewise for the cytosine/thymine polymorphism at position −509bp.

The invention further provides a diagnostic kit comprising a carrier means such as a box being compartmentalized to receive in close confinement therein the diagnostic means according to the second aspect of the invention, optionally within a container means such as a vial, tube, ampule, and the like. Further container means may also be present which comprise other elements of the diagnostic assay as described herein.

A third aspect of the invention provides DNA probes comprising a sequence selected from SEQ ID NO:s 1–4.

A fourth aspect of the invention provides a TGF-β1 gene in which a guanine nucleotide at position −800bp is replaced with an adenine nucleotide.

A fifth aspect of the invention provides a TGF-β1 gene in which a cytosine nucleotide at position −509bp is replaced with a thymine nucleotide.

According to the fourth and fifth aspects of the invention, it is preferred that the DNA molecule comprising said genes is in isolated form. The DNA molecules of the invention are considered to be isolated if they are free from their native environment. Preferably, the isolated DNA molecules are free from other nucleic acid molecules with which they are associated in nature or in known cDNA libraries. Isolated DNA molecules also include the DNA molecule when present in a cloning vector.

The present invention is based upon the discovery of a single base polymorphism in the TGF-β1 promoter. An aspect of the invention is that the polymorphism is correlated with a predisposition to a number of disease states including, in particular, atherosclerosis, cancers, osteoporosis, rheumatoid arthritis, multiple sclerosis, systemic lupus erythematosus, and other immune disorders. The invention is of advantage in that by screening for the presence of the polymorphism it is possible to identify individuals likely to have a genetic predisposition to one or more of these disease states.

Accordingly, a sixth aspect of the invention provides a method of therapy comprising screening an individual for a predisposition to osteoporosis and, if a genetic predisposition is identified, treating that individual to delay or reduce or prevent the osteoporosis.

A suitable treatment to prevent or reduce or delay osteoporosis is hormone replacement therapy. The use of this therapy is well known in the art. According to the invention, hormone replacement therapy can thus be commenced in individuals likely to have a predisposition to osteoporosis but in whom osteoporosis has not yet begun to any significant extent.

It is known that the use of hormone replacement therapy carries with it a concomitant increased risk of breast cancer. The invention offers the advantage that the increased risk of breast cancer associated with hormone replacement therapy can be accepted only by those women who are known to have a likelihood of predisposition to osteoporosis. In an embodiment of the sixth aspect of the invention, the predisposition of an individual to osteoporosis is assessed by determining whether that individual is homozygous for the wild type TGF-β1 gene, is heterozygous for the wild type and the polymorphism in which guanine at position −800bp is replaced by adenine, or is homozygous for the polymorphism.

According to the invention, an individual who is homozygous for the polymorphism is classified as being at highest risk. An individual being heterozygous is classified as having moderate risk. An individual being homozygous for the wild type TGF-β1 gene is classified as being in the lowest risk category.

Optionally, the assessment of an individual's risk factor is calculated by reference both to the presence of a TGF-β1 promoter polymorphism and also to other known genetic or physiological or dietary or other indications. The invention in this way provides further information on which measurement of an individual's risk can be based.

In a seventh aspect of the invention there is provided a method of therapy in which a predisposition of an individual to atherosclerosis is determined and then, if a predisposition is confirmed, that person is treated to prevent, reduce or delay atherosclerosis. The predisposition to atherosclerosis is assessed, in an embodiment of the invention, using the same criteria as for measurement of predisposition to osteoporosis in the above aspect of the invention. In an embodiment of the seventh aspect, the method comprises determining whether an individual has a predisposition to atherosclerosis and, treating an individual with such a predisposition to prevent, reduce or delay atherosclerosis. For example, the treatment could comprise alterations in that individual's diet. Another treatment could be pharmaceutical, such as by administration of an anticoagulant agent or a fibrinolytic agent. Specific treatments and methods are disclosed in U.S. Pat. Nos. 5,242,397 and 5,171,217, the contents of which are incorporated herein by reference.

In further aspects, the invention provides analogous therapies against cancer and auto-immune disorders, based upon identification of a TGF-β1 polymorphism correlated with a predisposition to these diseases. In the case of cancer, disease may result from either too much TGF-β or too little. Consequently, one such polymorphism is replacement of a cytosine at position −509bp by thymine; another is replacement of a guanine at −800bp by an adenine. In the case of auto-immune disorders, expected to be associated with lowered TGF-β, the polymorphism at −800bp in which adenine replaces guanine would be correlated with predisposition to disease; the polymorphism at −509bp, in which thymine replaces cytosine would be negatively correlated with disease The concentration of transforming growth factor β (TGF-β) in circulating plasma has been correlated with the development of several major diseases, including atherosclerosis and certain forms of cancer. However, the mechanisms which control the concentration of TGF-β in plasma are poorly understood. The present invention is based upon our discovery that the concentration of TGF-β in plasma (active TGF-β plus plasma latent TGF-β forms) is predominantly (79%) under genetic control in 66 out of 71 pairs of monozygotic female twins who were post-menopausal. The concentration of active TGF-β was also significantly under genetic control (57%). Analysis of the TGF-β1 promoter by single strand conformational polymorphism (SSCP) mapping has identified a single base polymorphism (A/G at position −800bp) which is significantly associated (p<0.01; n=276) with lower levels of TGF-β in plasma. These data suggest that predisposition to atherosclerosis or various forms of cancer may be linked to particular alleles within the TGFb1 locus.

TGF-β is a multifunctional cytokine which regulates the proliferation and differentiation of a wide variety of cell types in vitro. Recently, pathological misregulation of the TGF-β system has been implicated in the development of several major diseases, including various forms of cancer, atherosclerosis and fibrotic disease. Moses and colleagues showed that local expression of a constitutively active TGF-β1 transgene prevented the development of mammary carcinoma induced either by transgenic overexpression of TGF-α or by the chemical carcinogen DMBA ((1995) *Proc. Natl. Acad. Sci USA* 92). Similarly, studies from the groups of Akhurst and Balmain have demonstrated that low levels of TGF-β1 staining is prognostic for a high risk of malignant conversion of benign tumors in the p53 knockout mouse ((1994) *Cancer Res.* 54, 5831–5836). More recently, Markowitz et al., *Science* 268:1336–1338, 1995, have identified somatic mutations of the TGF-β type II signaling receptor, which would be likely to render it non-functional, in human colon cancer biopsies. These data suggest that local decreases in TGF-β activity may be involved in transformation to the malignant phenotype in vivo. By contrast, Arteaga et al., *J. Clin. Invest.* 92:2569–2576 (1995), have shown that transfecting a transformed cell line with a construct expressing active TGF-β rendered the cells more tumorigenic in vivo, probably because TGF-β is immunosuppressive and immune surveillance was compromised. Consistent with this observation, elevated levels of plasma TGF-β in patients with malignant prostatic tumours and hepatocellular carcinoma have been reported. While local suppression of TGF-β activity may result in malignant conversion, elevated plasma levels of TGF-β are correlated establishment of the tumor.

In studies on the role of TGF-β in atherogenesis, we have shown that mice expressing the apolipoprotein(a) transgene develop diet-induced lipid lesions resembling early human atherosclerotic plaques at sites in the vessel wall where TGF-β activity is locally depressed by high concentration of apolipoprotein(a). It has also been shown that tamoxifen, which elevates TGF-β activity both in the vessel wall and serum of mice, will prevent diet-induced lipid lesion formation in both apolipoprotein(a) mice and in C57B16 inbred mice. Consistent with these observations we have shown that the concentration of active TGF-β is depressed by five fold in individuals with severe coronary atherosclerosis compared to individuals with normal coronary arteries determined by angiography. Taken together, these studies suggest that decreased TGF-β activity, either in the vessel wall or in the circulation, is an important step in the development of atherosclerosis. Despite these correlations with major diseases, the mechanisms which control the concentration of TGF-β in circulating plasma are poorly understood. In the present invention we have examined whether there is genetic regulation of plasma TGF-β concentrations.

TGF-β protein in man is derived from three unlinked genetic loci, TGFb 1, TGFb2 and TGFb3 which express three protein isoforms TGF-β1, β2 and β3. Studies using isoform-specific ELISA assays have demonstrated that TGF-β2 is not present in human blood and TGF-β3 has been detected in platelet-poor plasma and serum from only 2/22 individuals tested (unpublished observations of the inventors). Most or all of the TGF-β present in blood from most individuals is therefore the b1 isoform. Recent studies have shown that TGF-β1 in blood is present in several different protein complexes. The highest concentrations of TGF-β1 are contained in the platelets, where it is present as two distinct platelet latent complexes, termed large and small latent complexes, which have no known biological activity. In contrast, platelet-poor plasma contains a biologically active form of TGF-β1 and a latent complex, which is distinct from either of the platelet latent complexes, that we have termed plasma latent complex. The same forms of plasma TGF-β are present in serum, together with much larger concentrations of platelet large latent complex which is released into serum when clotting occurs. For our present studies of the genetic control of plasma TGF-β in populations of twins, an ELISA was used which detects only the two forms of plasma TGF-β described above: the active form together with the plasma latent complex. The capture antibody (BDA 19; R&D Systems) does not recognize the platelet large latent complex which is released into serum and consequently the BDA19 ELISA detects the same concentrations of TGF-β in plasma or serum prepared from the same blood sample.

Having now generally described the invention, the same will be more readily understood through reference to the following Examples which are provided by way of illustration, and are not intended to be limiting of the present invention, unless specified.

EXAMPLE 1

TGF-β was assayed by BDA19 ELISA in serum samples from 136 pairs of twins (71 monozygotic and 65 dizygotic pairs) to assess the genetic contribution to variation in TGF-β concentration. The concordance in concentration between the monozygotic siblings was very high (sn/mean= 16.9% ±2.3%; n=66) in 66/71 pairs. For each of the remaining five pairs, one sibling had an elevated level of circulating TGF-β which was higher than in any of the other 66 twin pairs and was more than five standard deviations from mean of the population as a whole. It is very likely that these individuals had elevated concentrations of circulating TGF-β due to environmental influences and these five twin pairs were excluded from further analysis. For the remaining monozygotic twin pairs, the intraclass correlation coefficient ($r^2$MZ) was 0.79 (FIG. 1A).

Using the same exclusion criteria for the dizygotic twins, there were two twin pairs in which one sibling had a concentration of TGF-β greater than for any of the concordant monozygotic twin pairs and more than five standard deviations from the mean of the whole population. For the remaining 63 dizygotic pairs the correlation was less marked (intraclass correlation coefficient $r^2$D2=0.39; FIG. 1B) than for the monozygotic twin pairs. If genetic variation at a single locus were responsible for the variation in TGF-β concentration, the $r^2$DZ to $r^2$MZ ratio would be predicted to be 0.5 and as the number of unlinked alleles contributing to the control of TGF-β concentration increases, the $r^2$DZ to $r^2$MZ ratio decreases. In this study $r^2$MZ/$r^2$DZ=0.49, suggesting that genetic variability at very few unlinked loci, or possibly at only one locus, is responsible for the genetic control of circulating TGF-β.

The concentrations of active TGF-β in the serum samples were also measured using an ELISA in which the extracellular domain of the type II TGF-β receptor (R2X) is the capture agent. The concentration of active TGF-β in the circulation was also significantly correlated for the monozygotic twin pairs ($r^2MZ = 0.57$; FIG. 1C), but much less so in the dizygotic twins ($r^2DZ=0.11$; FIG. 1D). Since the $r^2DZ$ to $r^2MZ$ ratio is much lower than 0.5 we conclude that a number of unlinked genetic loci are likely to contribute to the variation in the concentration of active TGF-β. This is consistent with our previous observation that activation of TGF-β was inversely correlated with the concentration of lipoprotein(a), since the circulating concentration of Lp(a) is genetically determined at a locus unlinked to TGFb1.

Figure 2B:
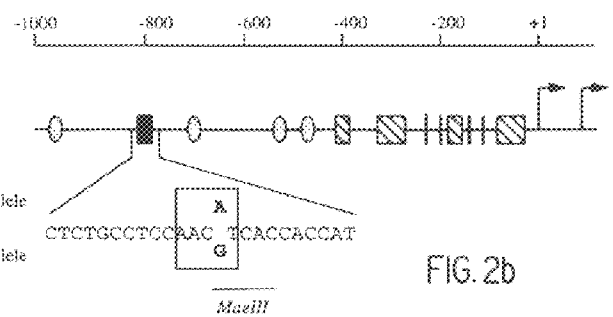

Since most of the TGF-β in plasma is the b1 isoform we investigated whether mutations at the TGFb1 locus influence the circulating concentration of TGF-β. Using SSCP mapping a polymorphism was identified in the promoter region of the TGFb1 gene approximately 1 kb upstream from the transcriptional start site (FIG. 2A, 2B). Sequencing of the PCR fragment analyzed by SSCP mapping identified the polymorphism as a single base change at position –800bp, with A replacing the G in the published genomic sequence (*J. Biol. Chem.* 264:402–408 (1989)) in approximately 10% of alleles. The presence of adenine at position –800bp destroyed a restriction site for the endonuclease maeIII which was therefore used to scan the promoter from the 136 twin pairs for the presence of this polymorphism. 52/276 individuals were heterozygous for this polymorphism and one monozygotic twin pair (2 individuals out of 276) were homozygous for A at position –800bp. The polymorphism was therefore present in this population at a frequency of 9.8% of alleles tested.

Figure 2C:
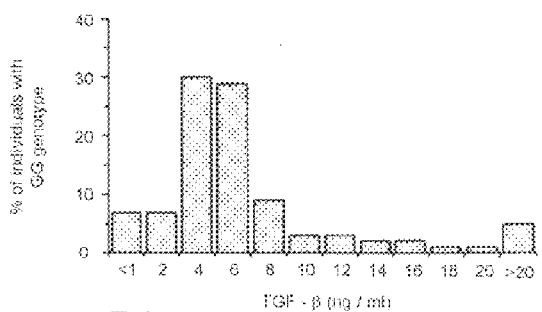
Figure 2D:
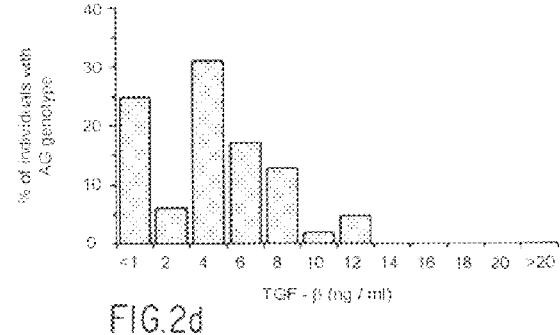

We tested whether the individuals with rare A allele had circulating levels of TGF-β significantly different from the more common G allele. The mean TGF-β serum concentration assayed by BDA19 ELISA in individuals with GG genotype was 6.4±0.6 ng/ml (n=252; FIG. 2C), not significantly different from the mean TGF-β concentration of 8.9±1.5 reported for a group of female donors of similar mean age. By contrast, the mean TGF-β concentration in individuals with AG genotype was 4.2±1.1 ng/ml ($p<0.01$; n=62; FIG. 2D). The siblings of the monozygotic twin pair homozygous for the A allele had TGF-β concentration of <1 ng/ml (below the detection limit of the assay used) and 2 ng/ml. Kruskal-Walis test for difference between GG and AG genotypes is $P=0.01$ taking all twins into account as independent individuals. We conclude that the presence of the A allele is significantly associated with lower circulating concentrations of TGF-β.

The polymorphism described is present in a consensus CREB half-site and the A allele would be expected to have reduced affinity for the CREB family of transcription factors. The polymorphism described may therefore be directly responsible for the different concentrations of TGF-β or alternatively it may be in linkage disequilibrium with other as yet unidentified polymorphisms in the TGFb1 locus which are affecting the concentration of TGF-β. Taken together, the data suggest that a major part of the genetic control over circulating levels of TGF-β may reside in the TGFb1 locus, since only a very few unlinked loci, or possibly only a single locus, are implicated in the control mechanism and we have identified a polymorphism in the TGFb1 locus which is correlated with TGF-β concentration.

EXAMPLE 2

The present Example follows on from the work reported in the first Example above.

Subjects

All the subjects tested here were female (age range 39 to 70 years; mean 57.7 years) and the majority were postmenopausal. Twins were recruited following a national media campaign and were broadly representative of the normal United Kingdom population. None of the subjects were taking hormone replacement therapy or other hormonally active medications. Serum was prepared and stored for TGF-β analysis. Lymphocyte DNA was also prepared for each subject using the standard phenol extraction method and zygosity status was determined by questionnaire and multiplex fingerprinting.

TGF-β analysis

Active plus acid-activatable latent (a+1) TGF-β was measured using the BDA19 capture ELISA. Active TGF-β was measured using the R2X capture ELISA. A single determination of each sample was made. The intra-assay co-efficient of variation of the assay used are 6.8% and 7.4% respectively. Serum samples with TGF-β concentration below the detection limit of the assays used (<1 ng/ml; 27/334 for (a+1) TGF-β and 37/334 for active TGF-β) were assigned a value of 0.5 ng/ml.

SSCP

Polymerase chain reaction (PCR) was used to amplify fragments of the promoter that were approximately 400bp long. 1.0 mg of genomic DNA was added to a 20 ml reaction consisting of 1×Taq Polymerase Buffer (Pharmacia), 50 nmol of each dNTP, and 6.25 pmol forward primer. The reaction was heated to 95 degrees C. for 30s and then held at 80 degrees C. while 5 ml containing 6.25 pmol reverse primer and 0.5 units Taq Polymerase in 1×Taq Polymerase Buffer was added. Samples were amplified for 35 cycles of 95 ITCH for 1 minute, 60 ITCH for 1 minute and 72 ITCH for 1 minute, followed by an extension period of 10 minutes at 72 ITCH. Primers were 5'-CCCGGCTCCATTTCCAGGTG-3' (SEQ ID NO: 1) and 5'-TGCTCTTGACCACTGTGCCA-3' (SEQ ID NO: 2) for G-800A polymorphism and 5'-CAGACTCTAGAGACTGTCAG-3' (SEQ ID NO: 3) and 5'-GGTCACCAGAGAAAGAGGAC-3' (SEQ ID NO: 4) for C-509T polymorphism. PCR products were denatured with 0.2M sodium hydroxide and 0.5 mM disodium ethylenediaminetetraacetic acid at room temperature. Single stranded DNA bands were resolved on a 20% acrylamide gel (Phastsystem, Pharmacia or XCell 11 system, R&D Systems) and visualized by silver staining.

Genotyping

G-800A polymorphism abolishes a Mae III restriction site. Mae III and Mae III Buffer (Boehringer) were added directly to the PCR products to a final volume of 30 ml, and incubated at 55 ITCH for 5 hours. Digests were resolved on a 1.2% agarose gel. C-509T polymorphism is in a Bsu 36 I restriction site. PCR products were precipitated with 3 volumes 96% ethanol and ¹⁄₁₀ volume 3 M sodium acetate pH 5.2 at –20 ITCH for 1 hour, followed by centrifugation at 13,000 r.p.m. for 10 mins. The DNA was resuspended in a 20 ml Bsu 36 I digest containing 10 units Bsu 36 I (New England Biolabs) and incubated at 37 ITCH for a minimum of 12 hours. Digests were resolved by 1.5% agarose gel electrophoresis.

TGF-β was assayed by BDA19 ELISA in serum samples from 174 pairs of twins (87 monozygotic (MZ) and 87 dizygotic (DZ) pairs) to assess the genetic contribution to variation in TGF-β concentration. The baseline characteristics of these twins are shown in Table 1. The MZ twins were slightly older than the DZ twins (mean age 58.9 years versus 56.6 years) and a significantly higher proportion were post-menopausal (87% versus 75%). However, neither of these variables were significantly associated with the concentration of (a+1) or active TGF-β. Consistent with our previous studies, the plasma (a+1) TGF-β concentrations of this population did not conform to a normal distribution. A boxcox transformation was applied to maximize normality, which resulted in equal means and variances between the MZ and DZ groups but the distributions remained significantly non-normal. We therefore treated TGF-β concentration as a categorical variable, assigning each individual into an approximate tertile (for (a+1) TGF-p these were 'low', less than 4 ng/ml; 'middle' 4–5 ng/ml; 'high' more than 5 ng/ml). For (a+1) TGF-β, the percent concordance (that is the proportion of twin pairs where both individuals fell into the same tertile) for MZ pairs (57.8%) was significantly higher than for DZ pairs (40.5%; p=0.025; Chi-square test; Table 2). This demonstrates that the concentration of (a+1) TGF-β in plasma is influenced by genetic factors.

The concentrations of active TGF-β in the serum samples were also measured using an ELISA in which the extracellular domain of the type II TGF-β receptor (R2X) as the capture agent. The distribution of active TGF-β concentrations for both groups of twins were significantly different from a normal distribution, even after boxcox transformation, as for the distribution of (a+1) TGF-β concentrations. Treating the active TGF-β concentration as a categorical variable ('low' less than 3ng/ml; 'middle' 3 or 4 ng/ml; 'high' greater than 4 ng/ml), the percent concordance between tertiles was again significantly higher for MZ twins (62.8%) than for DZ twins (43.6%; p=0.016; Chi-square test; Table 2). It appears, therefore, that the concentration of active TGF-β in plasma is also under genetic control.

Figure 3:
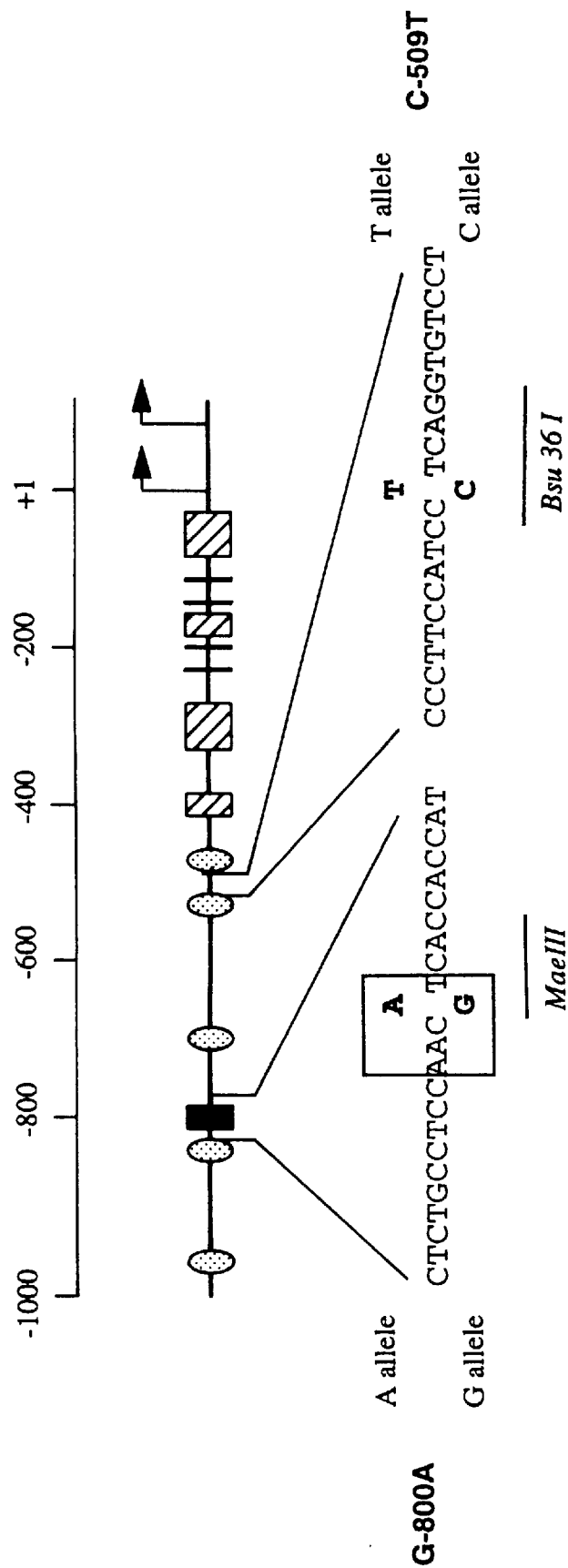
FIG. 3 shows the location of polymorphisms in the TGFb1 promoter. Diagrammatic representation of the putative transcription factor binding sites in the TGFb1 promoter. Hatched box: one or more consensus sp1 binding sites; vertical line : consensus ap2 binding site; stippled oval : consensus nuclear hormone binding element; filled box: consensus CREB half-site. The sequence of the CREB half-site is shown (boxed) with the single base polymorphism at −800bp marked in bold script. The maeIII consensus sequence present in the G allele (GTNAC) is underlined. The sequence surrounding the single base polymorphism at −509bp (bold script) is also shown (SEQ ID NOS: 5–8). All nucleotide positions are related to the most 5' transcriptional start site of the TGFb1 gene.

Since most of the TGF-β in plasma is the TGF-β1 isoform we investigated whether mutations at the TGFb1 locus influence the circulating concentration of TGF-β. Using SSCP analysis two polymorphisms were identified in the promoter region of the TGFb1 gene within 1.5 kbp upstream from the major transcriptional start site. Sequencing of the PCR fragments analyzed by SSCP mapping identified two single base substitution polymorphisms. The first polymorphism occurred at −800bp, with adenine replacing guanine in the published genomic sequence in approximately 10% of alleles (G-800A; FIG. 3). The second polymorphism was at −509bp with thymine replacing cytosine in approximately 30% of alleles (C-509T; FIG. 3). The genotype at these two sites in the TGFb1 promoter region was determined for the majority of the individuals in the twin study. For the G-800A polymorphism we found 59/341 individuals were heterozygous (AG) and two individuals (one monozygotic twin pair) were homozygous AA, corresponding to an A allele frequency of 0.092 in this population. For the C-509T, 160/330 individuals were heterozygous (CT), and 24/330 individuals were homozygous for thymine at this position (T allele frequency=0.315). The G-800A polymorphism is in Hardy-Weinberg equilibrium within the twin study (c2=0.345, p=0.557), however the C-509T polymorphism does not exhibit Hardy-Weinberg equilibrium when all twins are included (c2=5.012, p=0.025).

Figure 4A:
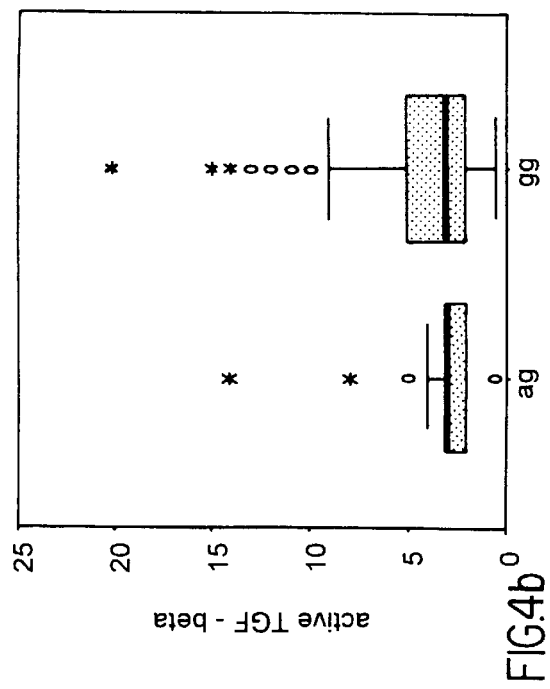
FIGS. 4A–4D shows association between polymorphisms in the TGFb1 promoter region and circulation concentration of TGF-β Boxplots (inter-quartile range) of (a+1) (4A, 4C) TGF-β concentrations and active (4B, 4C) TGF-β concentrations in groups of subjects sorted by genotype at −800bp (4A, 4B) and −509bp (4C, 4D).
Figure 4B:
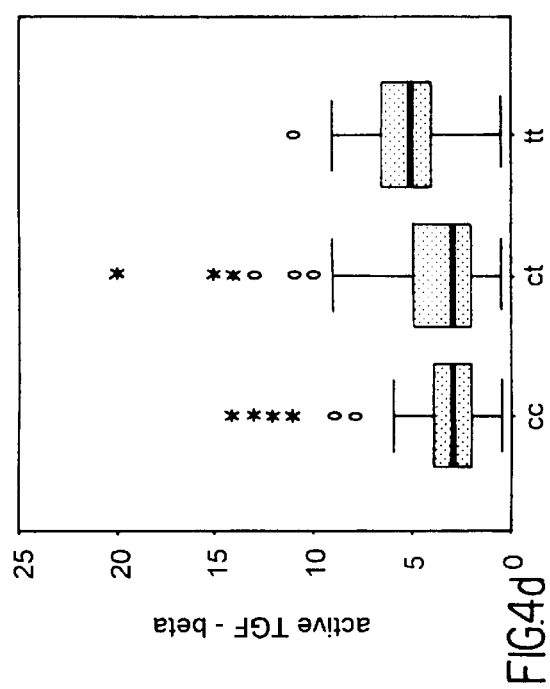
Figure 4C:
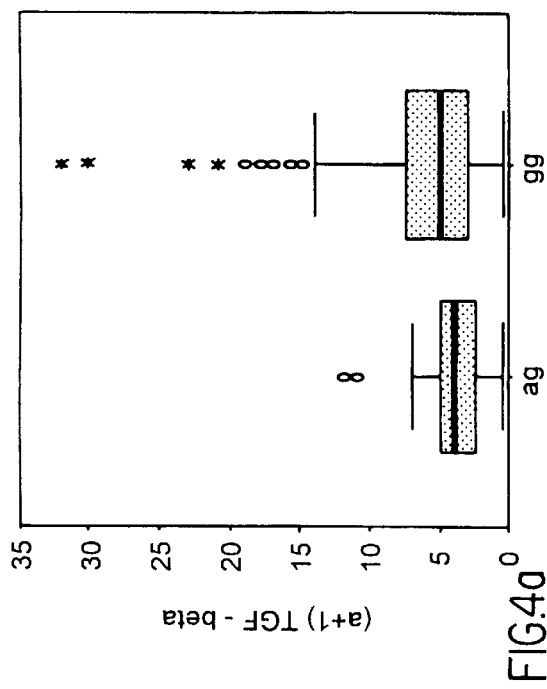

We tested whether there was any association between the TGFb1 promoter genotype and plasma concentration of (a+1) TGF-β. The presence of an A allele is significantly associated with lower circulating concentrations of TGF-β, irrespective of whether all individuals are included (tied p=0.0005; n =328; Kruskal-Wallis test) or if only one individual selected at random is included from each twin pair (tied p=0.02; n=164; Kruskal-Wallis test; FIG. 4A). The presence of the T allele at −509bp is significantly associated with higher plasma concentrations of TGF-β (tied p=0.0004; n=319; Kruskal-Wallis test), and this association is still significant if only one twin from each pair is included in the analysis (tied p=0.016, Kruskal-Wallis test; FIG. 4C). The G-800A and C-509T mutations are in repulsion, as genotypes such as AGTT, which would require adenine and thymine to be in linkage have never been observed.

Figure 4D:
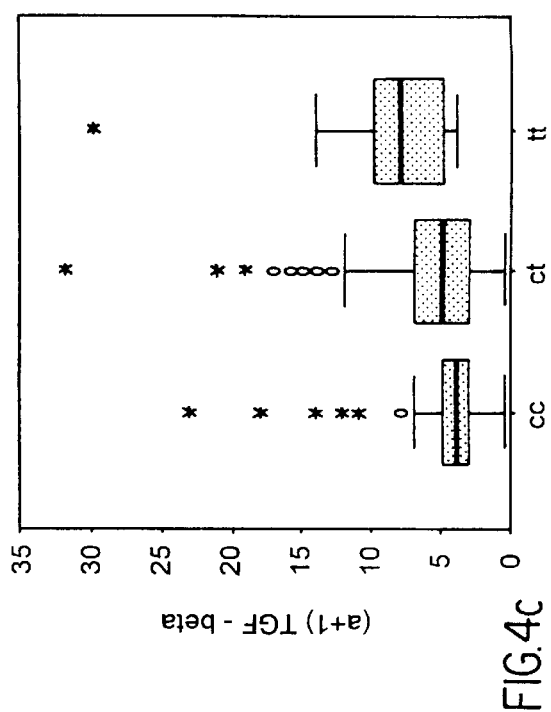

It was observed that (FIG. 4B, 4D) the T allele at −509bp is significantly associated with higher concentrations of active TGF-β (p=0.023; Kruskal-Wallis test with only one twin from each pair included) and the A allele −800bp is likely to be associated with lower concentrations of active TGF-β (p=0.076; Kruskal-Wallis test with only one twin from each pair included).

The presence of polymorphisms in the TGFb1 locus may indicate predisposition to diseases that have been linked to circulating levels of TGF-β, including atherosclerosis (decreased circulating TGF-β1) and some forms of cancer (elevated circulating TGF-β1).

The invention thus provides method and apparatus for identification and treatment of individuals having a TGF-β1 polymorphism, correlated with a predisposition to certain disease states.

TABLE 1

|  | MZ (n = 174) | DZ (n = 174) | p |
|---|---|---|---|
| Age (years) | 58.9 ± 6.6 | 56.6 ± 8.3 | 0.006 |
| Height (cm) | 160.2 ± 6.1 | 161.3 ± 5.9 | 0.078 |
| Weight (kg) | 62.9 ± 9.7 | 65.0 ± 1.0 | 0.063 |
| No. (%) post-menopausal | 131 (87) | 112 (75) | 0.007 |
| No. (%) current smoker | 24 (14) | 33 (19) | 0.325 |
| No. (%) on no alcohol | 23 (13) | 15 (9) | 0.121 |
| No. (%) previous HRT use | 32 (18) | 31 (18) | 0.889 |
| No. (%) hysterectomy | 35 (20) | 37 (21) | 0.791 |

Baseline characteristics of population. Only age and the number of post-menopausal individuals differed between the monozygous (MZ) and dizygous (DZ) groups (p values highlighted in bold). None of the individuals studied were currently on hormone-replacement therapy or taking other hormonally active medications. Abbreviation: HRT, hormone replacement therapy.

TABLE 2

|  |  |  | (a) (a + 1) TGF-β TWIN 2 | | |
|---|---|---|---|---|---|
|  |  |  | 'Low' | 'Middle' | 'High' |
| T W I N 1 | 'Low' | MZ | 12% | 12% | 4% |
|  |  | DZ | 11% | 14% | 5% |
|  | 'Middle' | MZ | 4% | 17% | 17% |
|  |  | DZ | 11% | 17% | 13% |
|  | 'High' | MZ | 2% | 4% | 29% |
|  |  | DZ | 6% | 11% | 13% |

|  |  |  | (b) active TGF-β TWIN 2 | | |
|---|---|---|---|---|---|
|  |  |  | 'Low' | 'Middle' | 'High' |
| T W I N 1 | 'Low' | MZ | 12% | 5% | 4% |
|  |  | DZ | 18% | 14% | 3% |
|  | 'Middle' | MZ | 6% | 30% | 14% |
|  |  | DZ | 8% | 18% | 12% |
|  | 'High' | MZ | 3% | 5% | 22% |
|  |  | DZ | 8% | 12% | 8% |

Within-pair concordance of (a+1) and active TGF-β concentrations between MZ and DZ twin pairs. The concentration of (a+1) (a) or active (b) TGF-β was treated as a categorial variable, and individuals assigned to approximate tertiles (for (a+1) TGF-β: 'low', <4 ng/ml; 'middle' 4–5 ng/ml; 'high' >5 ng/ml and for active TGF-β: 'low', <3 ng/ml; 'middle' 3–4 ng/ml; 'high' >4 ng/ml). The percentage of twin pairs in each of the MZ and DZ groups are shown separately for each combination of TGF-β concentration categories. The percentage pairwise concordance for each group is the proportion of twin pairs on the diagonal of each table. The percentage pairwise concordance is significantly higher from MZ than DZ twins for both (a+1) TGF-β ($p=0.025$; Chi-square test) and active TGF-β ($p=0.016$; Chi-square test). Where the proportion of twins in the cell differs significantly between the MZ and DZ groups ($p<0.05$; Chi-square test) the percentages are highlighted in bold.

All patents, patent applications and publications mentioned hereinabove are hereby incorporated by reference in their entirety.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of diagnosis of a disease or of a predisposition to a disease comprising detecting a polymorphism in a TGF-β1 promoter which is correlated with an increase or decrease in plasma TGF-β1 levels, wherein said disease is selected from the group consisting of osteoporosis, atherosclerosis, cancer and immune disorders and wherein detection of said polymorphism is indicative of the occurrence of said disease or predisposition to said disease.

2. The method of diagnosis of claim 1 comprising determining whether an individual possesses a wild type TGF-β1 promoter.

3. The method of diagnosis of claim 1 comprising determining whether an individual possesses a wild type TGF-β1 promoter or a variant promoter that differs from the wild type by at least a single nucleotide substitution.

4. The method of diagnosis of claim 3 wherein the variant differs from the wild type in that cytosine at position −509bp is substituted by thymine.

5. The method of diagnosis of claim 3 wherein the variant differs from the wild type in that guanine at position −800bp is substituted by adenine.

6. The method of claim 1 comprising amplifying said TGF-β1 promoter using PCR techniques.

7. Diagnostic means comprising PCR primers adapted to amplify a region of a TGF-β1 promoter, wherein said PCR primers are selected from the group consisting of (i) SEQ ID NO: 1 and SEQ ID NO: 2, and (ii) SEQ ID NO: 3 and SEQ ID NO: 4.

8. The diagnostic means of claim 7, further comprising a restriction endonuclease capable of cleaving a wild type TGF-β1 promoter at position −800bp and not capable of cleaving a variant of the wild type promoter in which the nucleotide at position −800bp is adenine.

9. The diagnostic means of claim 7, further comprising a restriction endonuclease capable of cleaving a wild type TGF-β1 promoter at position −509bp and not capable of cleaving a variant of the wild type promoter in which the nucleotide at position −509bp is thymine.

10. A DNA molecule comprising a TGF-β1 gene in which guanine at position −800bp is substituted by adenine.

11. A DNA molecule comprising a TGF-β1 gene in which cytosine at position −509bp is substituted by thymine.

12. A method of osteoporosis therapy comprising: screening an individual for a genetic predisposition to osteoporosis by detecting the presence of a polymorphism at position −800 of the TGF-β1 promoter; and if such a predisposition is identified, treating that individual to prevent or reduce osteoporosis or to delay the onset of osteoporosis, wherein said predisposition to osteoporosis is correlated with a TGF-β1 promoter in which at position −800bp a guanine nucleotide is substituted by an adenine nucleotide.

13. The method of claim 12, comprising treating the individual by hormone replacement therapy.

14. A method of atherosclerosis therapy comprising:

screening an individual for a genetic predisposition to atherosclerosis by detecting the presence of a polymorphism at position −800 of the TGF-β1 promoter; and if such a predisposition is identified, treating that individual to prevent or reduce atherosclerosis or to delay the onset of atherosclerosis, wherein said predisposition to atherosclerosis is correlated with a TGF-β1 promoter in which at position −800bp a guanine nucleotide is substituted by an adenine nucleotide.

15. A method of cancer therapy comprising: screening an individual for a genetic predisposition to cancer by detecting the presence of a polymorphism at position −509 of the TGF-β1 promoter; and if such a predisposition is identified, treating that individual to prevent or reduce cancer or to delay the onset of cancer, wherein said predisposition to cancer is correlated with a TGF-β1 promoter gene in which cytosine at position −509bp is substituted by thymine.

16. A method of cancer therapy comprising:

screening an individual for a genetic predisposition to cancer by detecting the presence of a polymorphism at position −800 of the TGF-β1 promoter; and if such a predisposition is identified, treating that individual to prevent or reduce cancer or to delay the onset of cancer, wherein said predisposition to cancer is correlated with a TGF-β1 promoter in which at position −800bp a guanine nucleotide is substituted by an adenine nucleotide.

17. A method of immune disorder therapy comprising:

screening an individual for a genetic predisposition to immune disorder by detecting the presence of a polymorphism at position −509 of the TGF-β1 promoter; and if such a predisposition is identified, treating that individual to prevent or reduce immune disorder or to delay the onset of immune disorder, wherein said predisposition to immune disorder is correlated with a TGF-β1 promoter gene in which cytosine at position −509bp is substituted by thymine.

18. A method of immune disorder therapy comprising:

screening an individual for a genetic predisposition to immune disorder by detecting the presence of a polymorphism at position −800 of the TGF-β1 promoter; and if such a predisposition is identified, treating that individual to prevent or reduce immune disorder or to delay the onset of immune disorder, wherein said predisposition to immune disorder is correlated with a TGF-β1 promoter in which at position −800bp a guanine nucleotide is substituted by an adenine nucleotide.

19. A diagnostic kit comprising a carrier means being compartmentalized to receive in close confinement therein PCR primers selected from the group consisting of (i) SEQ ID NO: 1 and SE ID NO: 2, and (ii) SEQ ID NO: 3 and SEQ ID NO: 4.

* * * * *